United States Patent [19]

Patel

[11] 4,397,315

[45] Aug. 9, 1983

[54] DRESSING WITH TEMPERATURE PACK

[75] Inventor: Harish A. Patel, Crystal Lake, Ill.

[73] Assignee: The Kendall Company, Boston, Mass.

[21] Appl. No.: 302,917

[22] Filed: Sep. 16, 1981

[51] Int. Cl.³ .............................................. A61F 7/00
[52] U.S. Cl. .................................... 128/403; 128/402
[58] Field of Search ....................... 128/399, 402–403, 128/379, 384, 254, 258, 400–401

[56] References Cited

U.S. PATENT DOCUMENTS

| | | | |
|---|---|---|---|
| 1,567,931 | 12/1925 | Epler | 128/DIG. 23 |
| 2,573,791 | 11/1951 | Howells | 128/403 X |
| 3,175,558 | 3/1965 | Caillouette et al. | 128/254 X |
| 3,763,622 | 10/1973 | Stanley, Jr. | 128/403 X |
| 3,804,077 | 4/1974 | Williams | 128/403 X |
| 3,867,939 | 2/1975 | Moore et al. | 128/254 |
| 3,889,684 | 6/1975 | Lebold | 128/402 |
| 3,905,367 | 9/1975 | Dapcich | 128/379 X |
| 4,107,509 | 8/1978 | Scher et al. | 128/379 X |

FOREIGN PATENT DOCUMENTS 1383536  2/1975  United Kingdom ............... 128/403

Primary Examiner—Lee S. Cohen
Assistant Examiner—Angela D. Sykes
Attorney, Agent, or Firm—Powell L. Sprunger

[57] ABSTRACT

A dressing for the body of a patient comprising, an elongated pack to produce heat or cold. The pack has a front surface and a rear surface. The dressing has an absorbent medium at least substantially covering the front and rear surface of the pack.

10 Claims, 3 Drawing Figures

U.S. Patent  Aug. 9, 1983  4,397,315
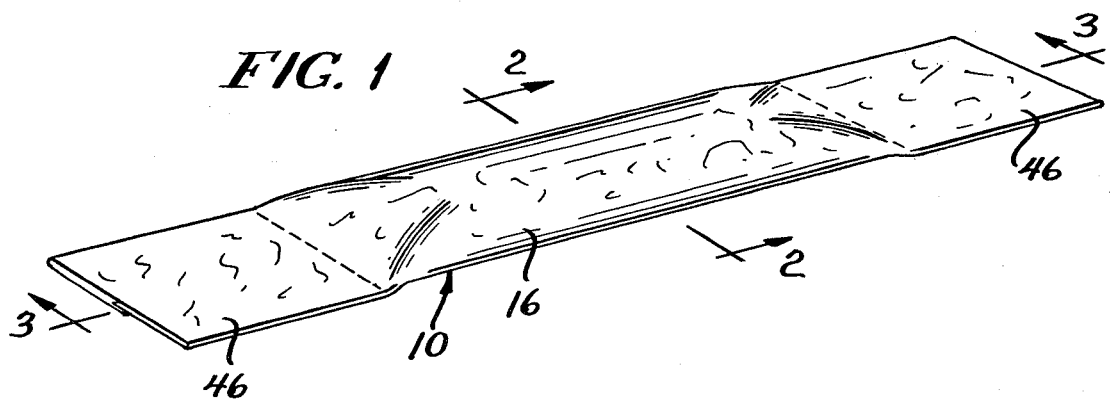
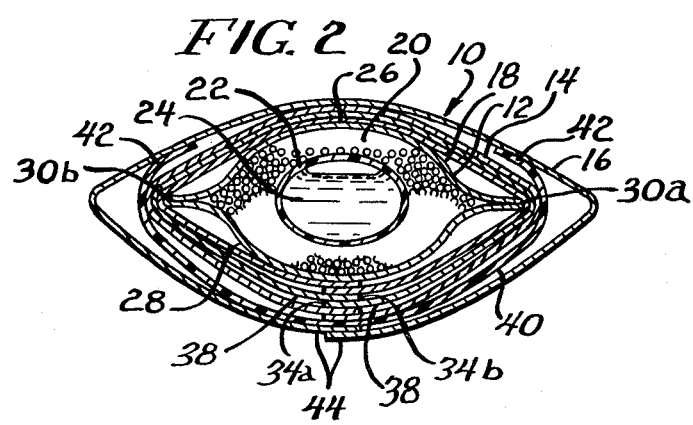
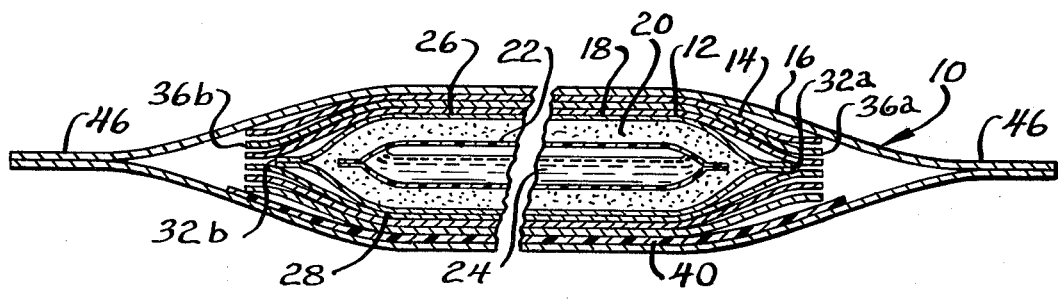

DRESSING WITH TEMPERATURE PACK

BACKGROUND OF THE INVENTION

The present invention relates to dressings for the body of a patient.

After childbirth, it is desirable to apply cold to the perineum of the patient for a period of 12 to 18 hours in order to prevent edema and pain. After the cold application period has expired, it is then desirable to apply heat to the perineum in order to dilate the blood vessels and enhance healing.

SUMMARY OF THE INVENTION

A principal feature of the present invention is the provision of an improved dressing for the body of a patient.

The dressing of the present invention comprises, an elongated pack having a front surface and a rear surface. The pack has absorbent means at least substantially covering the front and rear surface of the pack.

A feature of the present invention is that the pack produces heat or cold for the patient's body.

Another feature of the present invention is that the absorbent means covering the front surface of the pack separates the pack from direct contact with the patient's body which otherwise might be uncomfortable or damaging to the patient.

A further feature of the invention is that the absorbent means absorbs body fluids over the front surface of the pack, and transfers the body fluids to the absorbent means covering the rear surface of the pack for retention therein.

Yet another feature of the invention is that the dressing may have a fluid impervious sheet covering the absorbent means over the back surface of the pack in order to prevent leakage from the dressing.

Further features will become more fully apparent in the following description of the embodiments of this invention and from the appended claims.

DESCRIPTION OF THE DRAWINGS

In the drawings:

FIG. 1 is a perspective view of the dressing of the present invention;

FIG. 2 is a sectional view taken substantially as indicated along the line 2—2 of FIG. 1; and FIG. 3 is a fragmentary sectional view taken substantially as indicated along the line 3—3 of FIG. 1.

DESCRIPTION OF THE PREFERRED EMBODIMENTS

Referring now to FIGS. 1-3, there is shown a dressing generally designated 10 comprising an inner elongated pack 12, an intermediate set of a plurality of sheets 14 of absorbent tissue papers, and an outer sheet 16 of absorbent nonwoven material. The pack 12 has an outer envelope 18 of fluid impervious material, such as a suitable plastic material, with the outer envelope 18 defining a chamber 20. The pack 12 has an inner envelope 22 of fluid impervious material, such as a suitable plastic material, located in the chamber 20 of the outer envelope 18, with the inner envelope 22 defining a chamber 24. The walls of the inner envelope 22 are relatively thin, such that the inner envelope 22 may be ruptured during use of the dressing 10. For the production of heat, one of the chambers of the envelopes contains a suitable material, such as sodium thiosulphate, and the chamber of the other envelope contains a suitable material, such as ethylene glycol. For the production of cold, one of the chambers of the envelopes contains a suitable material, such as ammonium nitrate, and the other chamber of the envelopes contains a suitable material, such as water. The pack has a front surface 26 for facing the patient during use of the dressing 10, a rear or back surface 28 for facing away from the patient during use of the dressing 10, a pair of opposed side edges 30a, and 30b, and a pair of opposed end edges 32a and 32b connecting the side edges 30a and b.

The sheets 14 of absorbent tissue papers have a pair of opposed side edges 34a and 34b, and a pair of opposed end edges 36a and 36b connecting the side edges 34a and b. The sheets 14 extend across and cover the front surface 26 of the pack 12, with opposed side margins 38 of the sheets 14 being located over the back surface 28 of the pack 12, such that the side edges 34a and b of the sheets 14 are located adjacent each other over the back surface 28 of the pack 12. Thus, the sheets 14 extend over the front surface 26 of the pack 12, around the side edges 30a and b of the pack 12 to the back surface 28 of the pack 12, as shown. In one form, the tissue sheets 14 may be treated or coated with a superabsorbent or hydrocolloid material, such as an acrylic copolymer, preferably beneath the back surface of the pack.

The dressing 10 may have a sheet 40 of fluid impervious material, such as polyethylene, covering the sheets 14 over the back surface 28 of the pack 12. As shown, the sheet 40 of fluid impervious material may extend past the side edges 30a and b of the pack 12, with opposed side margins 42 of the sheet 40 being located over the front surface 26 of the pack 12 adjacent the side edges 30a and b of the pack 12.

The sheet 16 of nonwoven material extends completely around the sheets 14 and pack 12, and the sheet 16 may have opposed side margins 44 overlapping each other over the back surface 28 of the pack 12. As shown, the sheet 16 extends past the end edges 32a and b of the pack 12 and past the end edges 36a and b of the sheets 14 in order to define a pair of opposed end tabs 46 at the ends of the dressing 10.

In use, the dressing 10 is selected with a suitable pack 12 according to whether it is desirable to produce heat or cold. The dressing 10 is pressed by the user's fingers until the inner envelope 22 of the pack 12 is ruptured, after which the dressing 10 may be shaken to mix the materials in the chambers 20 and 24 of the pack 12 after which the pack 12 generates heat or cold depending upon the selected dressing. The dressing 10 is then placed against the perineum of the patient, such as after childbirth, and the dressing is held in place by use of a belt which is attached to the tabs 46 of the dressing 10.

During use of the dressing 10, body fluids of the patient pass through the sheet 16 of nonwoven material into the sheets 14 of absorbent tissue papers over the front surface 26 of the pack 12, after which the body fluids are transferred by the sheets 14 around the side edges 30a and b of the pack 12 to the portion of the sheets 14 underlying the back surface 28 of the pack 12 for retention therein. The sheet 40 of fluid impervious material prevents leakage of the body fluids from the sheets 14 where the fluids are retained. During use of the dressing 10, the sheets 14 of absorbent tissue papers and the sheet 16 of nonwoven material separate the pack 12 from direct contact with the patient's body in order to prevent discomfort or damage to the patient's body by the hot or cold pack 12. Also, during use of the dressing 10, the sheets 14 and 16 stabilize and maintain the pack 12 within the dressing 10.

The foregoing detailed description is given for clearness of understanding only, and no unnecessary limitations should be understood therefrom, as modifications will be obvious to those skilled in the art.

I claim:

1. A dressing for the body of a patient, comprising: an elongated pack to produce heat or cold, said pack having a front surface, a rear surface, and two opposed side edges, said pack comprising an outer closed envelope of fluid impervious material containing a first material, said outer envelope preventing passage of the first material therethrough, and an inner rupturable envelope of fluid impervious material containing a second material; said first and second materials producing heat or cold when contact is made between the two materials; and a plurality of sheets of absorbent material covering the front surface of the pack and extending around both side edges of the pack to the rear surface of the pack.

2. The dressing of claim 1 wherein said sheets have opposed side edges, and in which the opposed side edges are located adjacent each other over the rear surface of the pack.

3. The dressing of claim 1 including a backing sheet of fluid impervious material covering the sheets over the rear surface of the pack.

4. The dressing of claim 3 wherein said fluid impervious sheet has opposed side margins located over the front surface of the pack adjacent the side edges of the pack.

5. The dressing of claim 1 including an outer sheet of absorbent nonwoven material extending completely around said sheets and pack.

6. The dressing of claim 5 wherein said pack has a pair of opposed end edges connecting the opposed side edges and said nonwoven sheet includes a pair of opposed end tabs extending past the end edges of the pack and said absorbent sheets.

7. The dressing of claim 1 wherein one of said materials is sodium thiosulphate, and the other of said materials is ethylene glycol.

8. The dressing of claim 1 wherein one of said materials is ammonium nitrate, and the other of said materials is water.

9. The dressing of claim 1 wherein said sheets include a superabsorbent material.

10. The dressing of claim 9 wherein said superabsorbent material is located over the rear surface of the pack.

* * * * *